United States Patent
Huang et al.

(10) Patent No.: US 9,482,609 B2
(45) Date of Patent: Nov. 1, 2016

(54) SILICON OIL SENSOR AND ELECTRIC POWER TERMINAL ASSEMBLY

(71) Applicants: Tyco Electronics (Shanghai) Co. Ltd., Shanghai (CN); Tyco Electronics Corporation, Berwyn, PA (US)

(72) Inventors: Zhongxi Huang, Shanghai (CN); Ting Gao, Paolo Alto, CA (US)

(73) Assignees: Tyco Electronics (Shanghai) Co. Ltd., Shanghai (CN); Tyco Electronics Corporation, Berwyn, PA (US)

( * ) Notice: Subject to any disclaimer, the term of this patent is extended or adjusted under 35 U.S.C. 154(b) by 0 days.

(21) Appl. No.: 14/815,106

(22) Filed: Jul. 31, 2015

(65) Prior Publication Data

US 2015/0338343 A1 Nov. 26, 2015

Related U.S. Application Data

(63) Continuation of application No. PCT/IB2014/058429, filed on Jan. 21, 2014.

(30) Foreign Application Priority Data

Feb. 1, 2013 (CN) .......................... 2013 1 0040832

(51) Int. Cl.
*G01N 33/28* (2006.01)
*G01N 21/41* (2006.01)
(Continued)

(52) U.S. Cl.
CPC ....... *G01N 21/4133* (2013.01); *G01F 23/2922* (2013.01); *G01F 23/2925* (2013.01);
(Continued)

(58) Field of Classification Search
CPC .................. G02B 2027/0178; G02B 27/0172; G02B 27/017; G02B 2027/014; G02B 27/0093; G02B 27/01; G02B 5/20; G02B 26/0808; G02B 27/0087; G02B 3/0006; G02B 3/0037; G02B 5/005; G02B 5/1814; G02B 5/1828
See application file for complete search history.

(56) References Cited

U.S. PATENT DOCUMENTS

| | | | | |
|---|---|---|---|---|
| 5,396,325 A | * | 3/1995 | Carome | G01N 21/648 356/128 |
| 2009/0039296 A1 | * | 2/2009 | Richard | G08B 29/046 250/576 |
| 2013/0016357 A1 | | 1/2013 | Cheim | |

FOREIGN PATENT DOCUMENTS

| | | |
|---|---|---|
| DE | 102005044157 A | 3/2007 |
| JP | 5575620 A | 6/1980 |

(Continued)

OTHER PUBLICATIONS

PCT International Search Report, International Application No. PCT/IB2014/058429, dated Jun. 23, 2014, 4 pages.

(Continued)

*Primary Examiner* — Michael P Stafira
(74) *Attorney, Agent, or Firm* — Barley Snyder

(57) ABSTRACT

A silicon oil sensor is provided and includes a transparent member and a laser source emitting a laser beam. The transparent member includes a light receiving passageway with an oil receiving section and a side surface. The laser beam is directed into the light receiving passageway such that an incident angle θ of the laser beam (L) with respect to the side surface is selected so that a total reflection of the laser beam (L) occurs on the side surface when the oil receiving section is filled with air and exits out of the transparent member along a total reflection path (L1). A refraction of the laser beam (L) occurs along a refraction path (L2) when the oil receiving section collects silicon oil.

14 Claims, 5 Drawing Sheets

(51) Int. Cl.
  *G01N 21/03* (2006.01)
  *G01M 3/04* (2006.01)
  *G01M 3/38* (2006.01)
  *G01F 23/292* (2006.01)

(52) U.S. Cl.
  CPC ............... *G01M3/047* (2013.01); *G01M 3/38* (2013.01); *G01N 21/0303* (2013.01); *G01N 2021/0389* (2013.01); *G01N 2201/06113* (2013.01)

(56) References Cited

FOREIGN PATENT DOCUMENTS

| | | |
|---|---|---|
| JP | 1265138 A | 10/1989 |
| JP | 628715 U | 4/1994 |

OTHER PUBLICATIONS

Abstract of JPS5575620A, dated Jun. 7, 1980, 2 pages.
Abstract of DE102005044157A1, dated Mar. 29, 2007, 1 page.
Abstract of JP1265138, dated Oct. 23, 1989, 2 pages.

\* cited by examiner

SILICON OIL SENSOR AND ELECTRIC POWER TERMINAL ASSEMBLY

CROSS-REFERENCE TO RELATED APPLICATION

This application is a continuation of PCT International Patent Application No. PCT/IB2014/058429 filed Jan. 21, 2014, which claims priority under 35 U.S.C. §119 to Chinese Patent Application No. 201310040832.1 filed on Feb. 1, 2013.

FIELD OF THE INVENTION

The present invention relates to a silicon oil sensor and, more particularly, to a silicon oil sensor for detecting silicon oil leaking out of an outdoor electric power terminal filled with the silicon oil.

BACKGROUND

An outdoor electric power terminal filled with silicon oil may be applied to a high voltage cable of, for example, 170 kV. However, there is a risk that the silicon oil may leak out of the outdoor electric power terminal and cause a serious power failure. Furthermore, the outdoor electric power terminal is often mounted high above the ground. Therefore, it is difficult to find the leaked silicon oil in time.

Known silicon oil sensors generally include a conductive layer directly formed by conductive particles or a porous material, for example, polytetrafluoroethylene (PTEE) filled by conductive particles. When the silicon oil flows to the conductive layer of the silicon oil sensor, the conductive particles directly contact the silicon oil and are wrapped by the silicon oil, resulting in changes of the electric resistance of the conductive layer. Thereby, it is possible to detect whether the silicon oil leaked of the outdoor electric power terminal based on the change of the electric resistance of the conductive layer of the silicon oil sensor. However, in the known silicon oil sensor, when the conductive particles are wrapped by the leaked silicon oil, the change of the electric resistance of the conductive layer is very slow and not significant, that is, this known silicon oil sensor has poor detection sensitivity and cannot detect the leaked silicon oil in time. As a result, it cannot reliably prevent the power failure due to the leaked silicon oil.

In order to overcome the disadvantages of the above known silicon oil sensor, Japanese Patent Document No.JP1265138A discloses a known fiber sensor for the silicon oil. The known fiber sensor includes a fiber core fixed on a surface of a plastic body. Once the silicon oil is dropped onto the fiber core, the fiber sensor can determine that the silicon oil is leaked out of the electric power terminal. However, in the known fiber sensor, the known fiber sensor is formed a plastic body by pouring polymer material on the fiber and polishing the plastic body until the fiber core of the fiber is exposed. As a result, the process of manufacture of the fiber sensor is very complicated and difficult. Additionally, the size of the fiber is very small and cannot detect a large area and, therefore, it needs an additional funnel to collect the leaked silicon oil within the large area. Furthermore, the known fiber sensor is also affected by rain water or other liquid like the silicon oil. As a result, it may mistake the rain water as the leaked silicon oil when it is used in the outdoor environment.

SUMMARY

The present invention has been made to overcome or alleviate at least one aspect of the above mentioned disadvantages. Accordingly, it is an object of the invention, among others to provide a silicon oil sensor having a transparent member and a laser source emitting a laser beam. The transparent member includes a light receiving passageway with an oil receiving section and a side surface. The laser beam is directed into the light receiving passageway such that an incident angle θ of the laser beam (L) with respect to the side surface is selected so that a total reflection of the laser beam (L) occurs on the side surface when the oil receiving section is filled with air and exits out of the transparent member along a total reflection path (L1). A refraction of the laser beam (L) occurs along a refraction path (L2) when the oil receiving section collects silicon oil.

BRIEF DESCRIPTION OF THE DRAWINGS

The above and other features of the present invention will become more apparent by describing in detail exemplary embodiments thereof with reference to the accompanying drawings, in which.

DETAILED DESCRIPTION OF THE EMBODIMENT(S)

Figure 1:
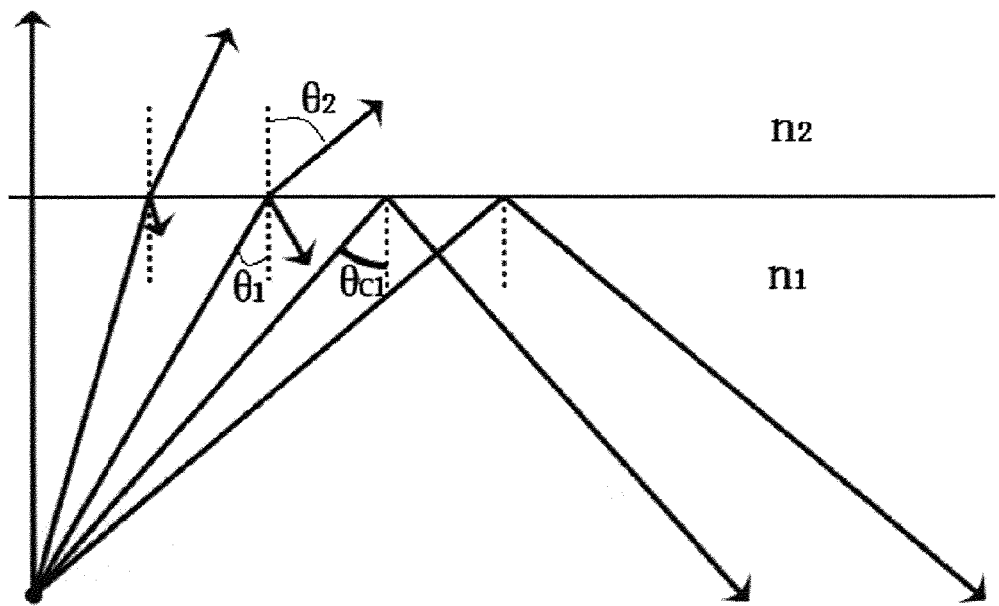
FIG. 1 is a schematic diagram showing total reflection of a light on an interface between two different mediums.

Exemplary embodiments of the present disclosure will be described hereinafter in detail with reference to the attached drawings, wherein the like reference numerals refer to the like elements. The present disclosure may, however, be embodied in many different forms and should not be construed as being limited to the embodiment set forth herein; rather, these embodiments are provided so that the present disclosure will be thorough and complete, and will fully convey the concept of the disclosure to those skilled in the art.

As shown in FIG. 1, when light is transmitted from an optically denser medium, for example, having a refractive index of n1, onto an interface between the optically denser medium and an optically thinner medium, for example, having a refractive index of n2 less than n1, the refractive angle θ2 is increased as the incident angle θ1 is increased. When the refractive angle θ2 is increased to 90 degrees or the incident angle θ1 of the light is increased to a critical angle θc1, a total reflection of the light occurs on the interface between the optically denser medium and the optically thinner medium. That is, when the incident angle θ1 of the light is equal to or larger than the critical angle θc1, a total reflection of the light occurs on the interface between the optically denser medium and the optically thinner medium. Refraction no longer occurs.

Herein, according to the above principle shown in FIG. 1, a silicon oil sensor according to the invention is provided.

Figure 2:
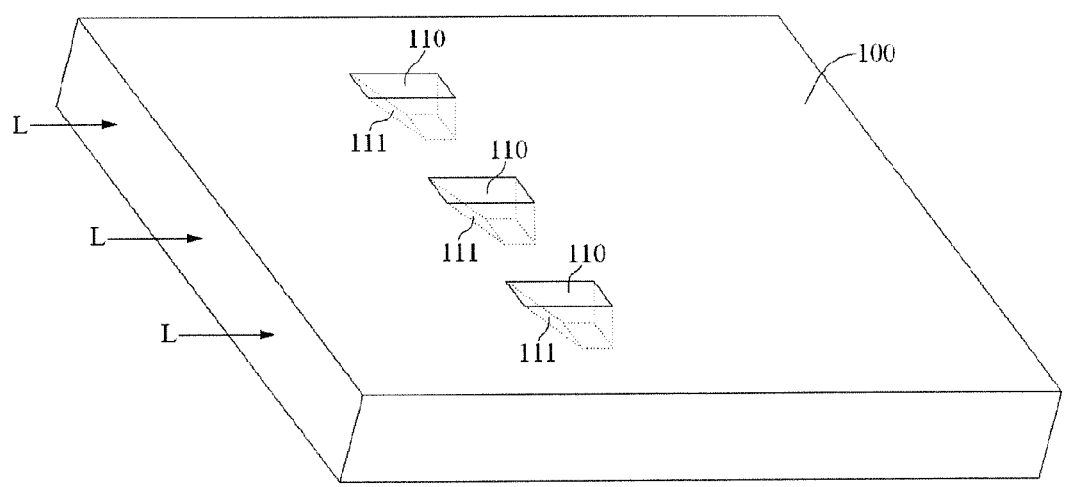
FIG. 2 is a schematic diagram of a silicon oil sensor according to the invention.
Figure 3:
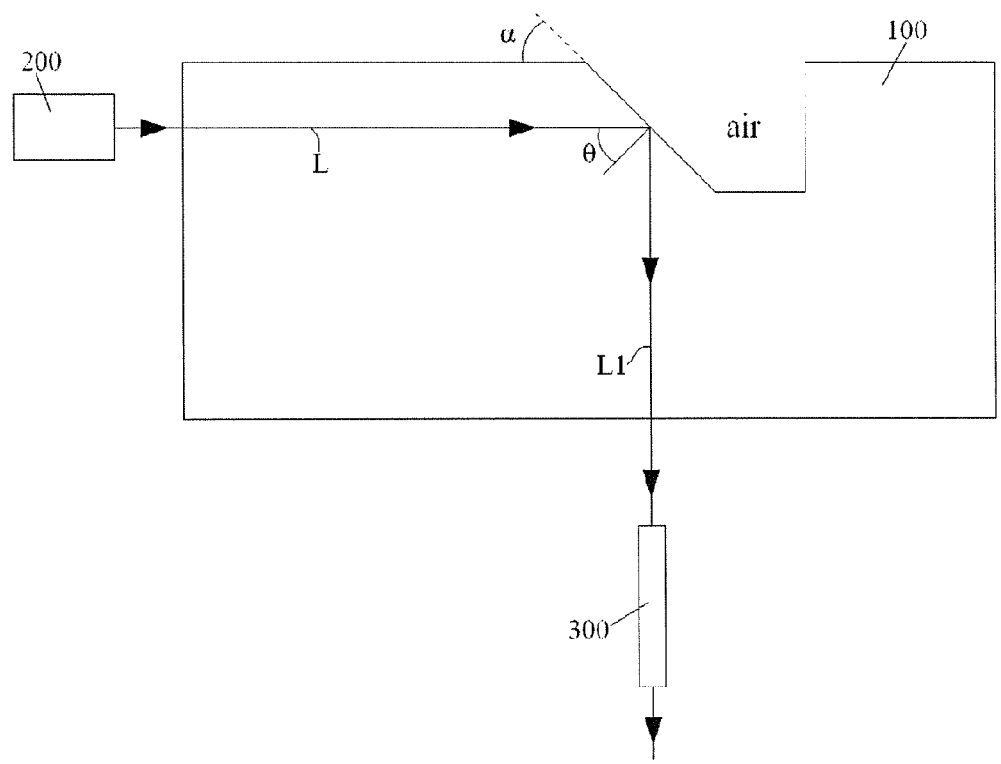
FIG. 3 is a schematic diagram of a silicon oil sensor according to the invention showing a transparent member with a light receiving passageway that is filled with air.

As shown in FIGS. 2 and 3, a silicon oil sensor is provided and includes a transparent member 100 made of a transparent material and a laser source 200 for emitting a laser beam L into the transparent member 100.

In an exemplary embodiment, as shown in FIG. 2, three light receiving passageways 110 are formed in the transparent member 100. The three light receiving passageways 110 are separated from each other and arranged in a row. Each of the light receiving passageways 110 has a side surface 111 facing the incident laser beam L emitted from the laser source 200. Thereby, the incident laser beam L can be irradiated on the side surface 111 of the light receiving passageway 110.

In an exemplary embodiment, as shown in FIGS. 2 and 3, the transparent member 100 is shaped into a cuboid block having a top surface, a bottom surface and four vertical side surfaces. The light receiving passageways 110 are formed in the top surface of the transparent member 100. The incident laser beam L is irradiated onto the side surface 111 of the light receiving passageway 110 in a horizontal direction. The side surface 111 is configured to have an angle $\alpha$ with respect to the horizontal top surface of the transparent member 100. The incident angle $\theta$ of the laser beam L with respect to the side surface 111 can be calculated by the expression: $\theta = 90° - \alpha$.

As shown in FIG. 3, in an exemplary embodiment, the refractive index n1 of the transparent material of the transparent member 100 may be selected to be larger than or less than the refractive index n2 of the silicon oil. Generally, the refractive index of the air is equal to 1, and the refractive index n2 of the silicon oil is larger than the refractive index of the air or 1.

Figure 4:
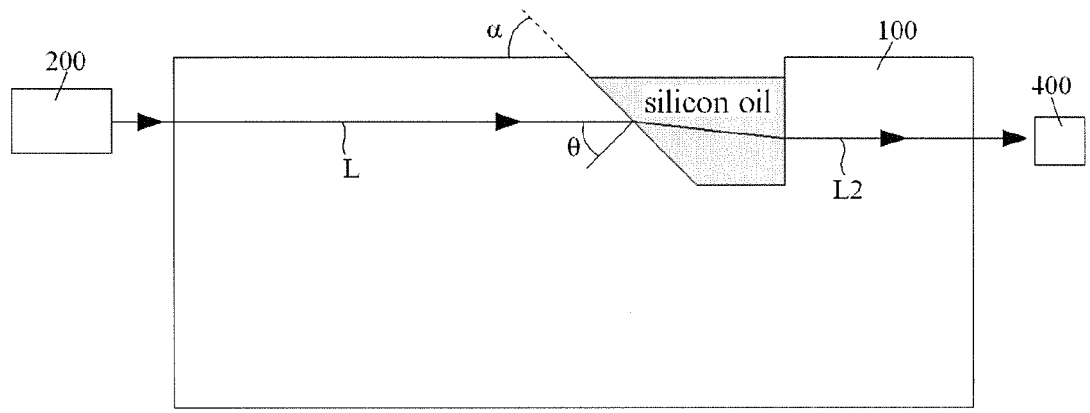
FIG. 4 is a schematic diagram of a silicon oil sensor according to the invention showing a transparent member with a light receiving passageway that is filled with oil.
Figure 4:
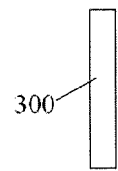

With reference to FIG. 4, another silicon oil sensor according to the invention is provided, wherein a light receiving passageway 110 of a transparent member 100 is filled with silicon oil.

As shown in FIGS. 3 and 4, in an exemplary embodiment, the incident angle $\theta$ ($=90°-\alpha$) of the laser beam L with respect to the side surface 111 is selected so that when the light receiving passageway 110 is filled with air (that is, the light receiving passageway 110 is empty), as shown in FIG. 3, a total reflection of the laser beam L occurs on the side surface 111 and exits out of the transparent member 100 in a total reflection path L1. Additionally, when the light receiving passageway 110 is filled with silicon oil, as shown in FIG. 4, refraction of the laser beam L occurs, instead of a total reflection on the side surface 111, and exits out of the transparent member 100 in a refraction path L2 different from total reflection path L1.

Accordingly, according to the invention, it can detect whether the silicon oil is leaked into the light receiving passageway 110 according to the path in which the laser beam L exits out of the transparent member 100.

As described the above, when total reflection of the laser beam L occurs on the side surface 111 and exits out of the transparent member 100 in a total reflection path L1, a light spot appears below the transparent member 100. When the leaked silicon oil is dropped into the light receiving passageway 110 of the transparent member 100, total reflection of the laser beam L does not occur on the side surface 111, and the light spot disappear below the transparent member 100. Therefore, an inspector can directly determine whether the silicon oil is leaked into the light receiving passageway 110 by viewing whether the light spot appears below the transparent member 100.

In an exemplary embodiment, when the refractive index n1 of the transparent material is larger than the refractive index n2 of the silicon oil, the incident angle $\theta$ of the laser beam L with respect to the side surface 111 is selected to satisfy a following expression:

$$\arcsin(1/n1) = \theta c1 \leq \theta < \theta c2 = \arcsin(n2/n1), \quad \text{Equation 1}$$

wherein, $\theta c1$ refers to a critical angle at which total reflection of the laser beam L directed into the transparent material occurs on an interface between the transparent material and the air, $\theta c2$ refers to a critical angle at which total reflection of the laser beam L directed into the transparent material occurs on an interface between the transparent material and the silicon oil, and the refractive index of the air is about equal to 1.

In an exemplary embodiment, when the refractive index n1 of the transparent material is less than the refractive index n2 of the silicon oil, the incident angle $\theta$ of the laser beam L with respect to the side surface 111 is selected to satisfy a following expression:

$$\arcsin(1/n1) = \theta c1 \leq \theta < 90. \quad \text{Equation 2}$$

Figure 5:
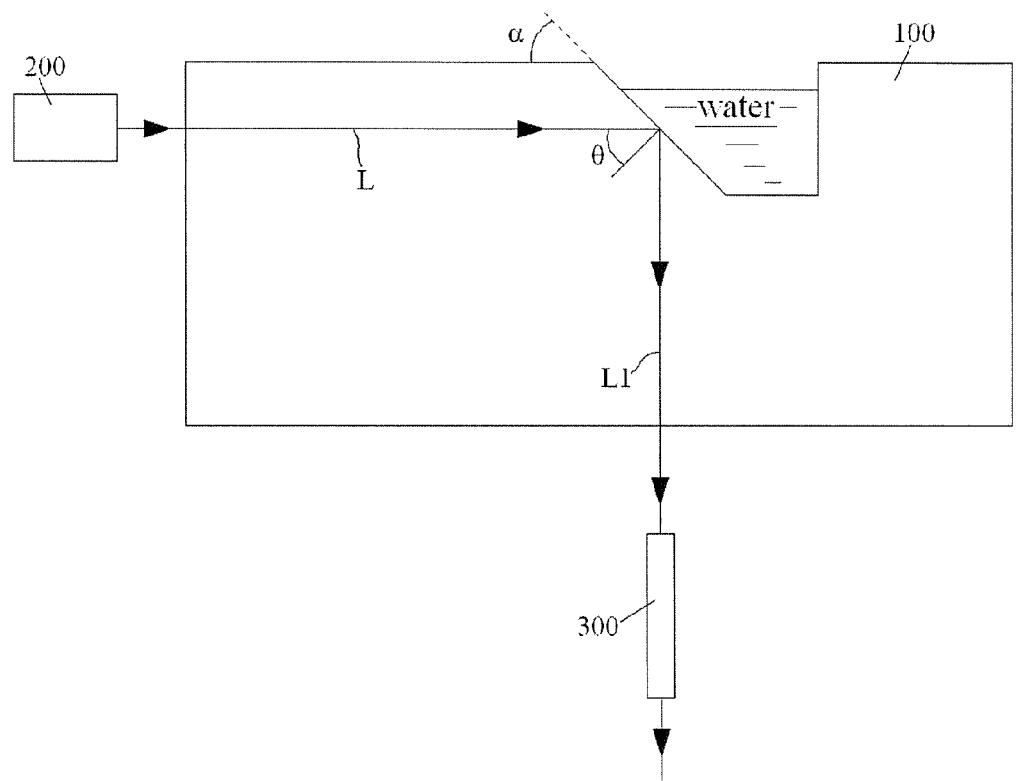
FIG. 5 is a schematic diagram of a silicon oil sensor according to the invention showing a transparent member with a light receiving passageway that is filled with water.

With reference to FIG. 5, a silicon oil sensor according to the invention is provided, wherein a light receiving passageway 110 of a transparent member 100 is filled with water.

In an exemplary embodiment, as shown in FIG. 5, the refractive index n1 of the transparent material and the incident angle $\theta$ of the laser beam L with respect to the side surface 111 are selected so that: when the light receiving passageway 110 is filled with water, as shown in FIG. 5, total reflection of the laser beam L occurs on the side surface 111 and exits out of the transparent member 100 in total reflection path L1. With this configuration, when the light receiving passageway 110 is filled with water, the silicon oil sensor according to the invention can prevent mistaking the water as the leaked silicon oil.

In an exemplary embodiment, when the refractive index n1 of the transparent material is larger than the refractive index n2 of the silicon oil, the incident angle $\theta$ of the laser beam L with respect to the side surface 111 is selected to satisfy a following expression:

$$\arcsin(n3/n1) = \theta c3 \leq \theta < \theta c2, \quad \text{Equation 3}$$

wherein, $\theta c3$ refers to a critical angle at which total reflection of the laser beam L directed into the transparent material occurs on an interface between the transparent material and the water, n3 refers to the refractive index of water, and the refractive index n3 of water is less than the refractive index n1 of the transparent material and the refractive index n2 of the silicon oil.

In an exemplary embodiment, when the refractive index n1 of the transparent material is less than the refractive index n2 of the silicon oil, the incident angle $\theta$ of the laser beam L with respect to the side surface 111 is selected to satisfy a following expression:

$$\arcsin(n3/n1) = \theta c3 \leq \theta < 90. \quad \text{Equation 4}$$

That is, in the above exemplary embodiment shown in FIG. 5, the refractive index n1 of the transparent material is selected to be larger than the refractive index n3 of the rain water. In this way, the invention can prevent mistaking the rain water as the leaked silicon oil.

In an exemplary embodiment, as shown in FIG. 2, the side surface 111 of the light receiving passageway 110 facing the incident laser beam L is configured as a slope side surface with respect to a horizontal direction or the top surface of the transparent member 100. But the invention is not limited to the shown embodiment and, in another embodiment, the side surface 111 of the light receiving passageway 110 facing the incident laser beam L may be configured as a vertical side surface with respect to a horizontal direction.

Although the inspector can simply determine whether the silicon oil is leaked into the light receiving passageway 110 by viewing whether the light spot appears below the transparent member 100, it is impossible that the inspector is always in the field. Therefore, in another exemplary embodiment, as shown in FIG. 3, the silicon oil sensor may further include a first light detection device 300. The first light detection device 300 may be disposed at a first position corresponding to total reflection path L1 below the transparent member 100 so as to receive the light of the laser beam led out the transparent member 100 in total reflection path L1. As a result, when the first light detection device 300 receives the light of the laser beam, it can determine that the silicon oil is not leaked into the light receiving passageway 110 of the transparent member 100. When the first light detection device 300 does not receive the light of the laser beam, it can determine that the silicon oil is leaked into the light receiving passageway 110 of the transparent member 100. In an exemplary embodiment, once the first light detection device 300 does not receive the light of the laser beam, an alarm is immediately provided by, for example, an acoustic alarm, an optical alarm, a vibration alarm, etc., so that an operator is notified to deal with the electric power terminal that has occurred silicon oil leakage.

In an exemplary embodiment, the first light detection device 300 may be an optical fiber, a light receiving device or other light sensitive elements.

In another exemplary embodiment, as shown in FIG. 4, the silicon oil sensor may further include a second light detection device 400. The second light detection device 400 is disposed at a second position corresponding to the refractive path L2 so as to receive the light of the laser beam led out the transparent member 100 in the refractive path L2. As a result, when the second light detection device 400 receives the light of the laser beam, it can determine that the silicon oil is leaked into the light receiving passageway 110 of the transparent member 100; when the second light detection device 400 does not receive the light of the laser beam, it can determine that the silicon oil is not leaked into the light receiving passageway 110 of the transparent member 100. In an exemplary embodiment, once the second light detection device 400 receives the light of the laser beam, an alarm is immediately provided by, for example, an acoustic alarm, an optical alarm, a vibration alarm, etc., so that an operator is notified to deal with the electric power terminal that has occurred silicon oil leakage.

In an exemplary embodiment, the second light detection device 400 may be an optical fiber, a light receiving device or other light sensitive elements.

It should be noted that the silicon oil sensor of the invention may include only one of the first and second light detection devices 300 and 400 or include both of the first and second light detection devices 300 and 400.

In a case where the silicon oil sensor includes both of the first and second light detection devices 300 and 400, it can determine whether the silicon oil is leaked into the light receiving passageway 110 according to detection results of both of the first and second light detection devices 300 and 400 rather than one detection result of only one of the first and second light detection devices 300 and 400. For example, when the first light detection device 300 receives the light of the laser beam and when the second light detection device 400 does not receive the light of the laser beam, it determines that the silicon oil is not leaked into the light receiving passageway 110 of the transparent member 100; when the first light detection device 300 does not receive the light of the laser beam and when the second light detection device 400 receives the light of the laser beam, it can determine that the silicon oil is leaked into the light receiving passageway 110 of the transparent member 100. In this way, it can improve the reliability and accuracy of detection on the silicon oil leakage.

In the shown embodiment of FIG. 2, a plurality of light receiving passageways 110 are formed in the transparent member 100, and the plurality of light receiving passageways 110 are separated from each other and arranged in a row. But the invention is not limited to the shown embodiment, there may be only a single elongate groove or a plurality of elongate grooves formed in the transparent member 100.

Figure 6:
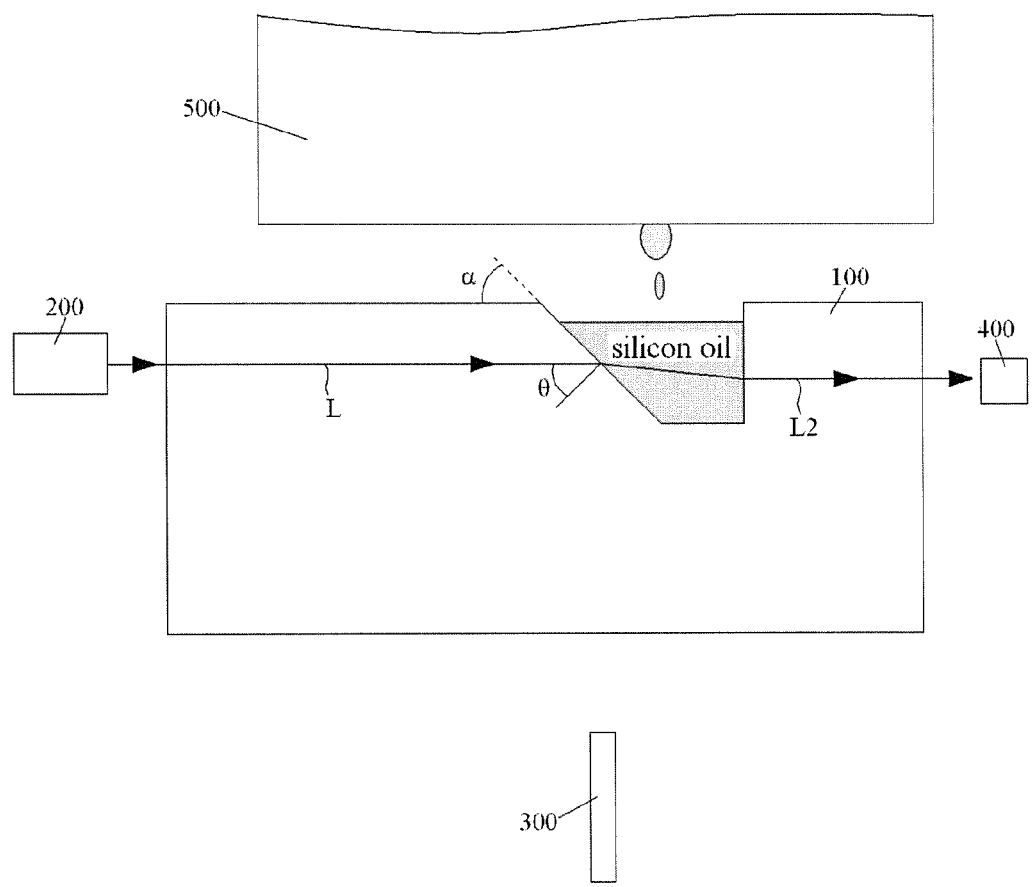
FIG. 6 is schematic diagram of an electric power terminal assembly according to the invention.

With reference to FIG. 6, an electric power terminal assembly according to the invention is shown.

As shown in FIG. 6, the transparent member 100 of the silicon oil sensor of FIG. 2 is disposed below an outdoor electric power terminal 500 filled with the silicon oil so as to detect whether the silicon oil is leaked out of the outdoor electric power terminal 500. In this way, the outdoor electric power terminal 500 and the silicon oil sensor are combined as an electric power terminal assembly.

In an exemplary embodiment, the sensor is not affected by the rain water, and the transparent member 100 of the silicon oil sensor may be directly exposed in an outdoor atmosphere environment without any waterproof film being formed thereon, as shown in FIG. 6.

In an exemplary embodiment, as shown in FIG. 6, the light receiving passageway 110 is formed in a trumpet shape and has a flared opening toward the outdoor electric power terminal 500 to receive the silicon oil leaked out of the outdoor electric power terminal 500. In this way, the trumpet-shaped light receiving passageway 110 can increase the detect area of the silicon oil sensor without needing an additional funnel to collect the leaked silicon oil.

In an exemplary embodiment, the size of the transparent member 100 and the size/the number of the light receiving passageways 110 may be determined based on the size of the outdoor electric power terminal 500. That is, the silicon oil sensor should be adapted to the outdoor electric power terminal 500 in size.

It should be noted that the shape of the light receiving passageway 110 is not limited to the shown embodiment, in another exemplary embodiment, a vertical section of the light receiving passageway 110 may have a shape of trapezoid (such as isosceles trapezoid), triangle or any other suitable shape.

In order to prevent mistaking the rain water as the leaked silicon oil, the refractive index n1 of the transparent material must be selected to be larger than the refractive index n3 of the rain water, but the refractive index n1 of the transparent material may be less than the refractive index n2 of the silicon oil. Therefore, the transparent material for forming the transparent member 100 may include at least one of glass, methyl methacrylate, polycarbonate, polystyrene, fluorinated ethylene propylene, epoxy resin and polyester.

The following table 1 shows several suitable transparent materials, respective refractive indexes n1, n2, n3 thereof, as well as respective critical angles $\theta c1$, $\theta c2$, $\theta c3$ thereof.

TABLE 1

| Transparent material | Refractive index n1 | θc1 (Refractive index of air is equal to 1) | θc3 (Refractive index n3 of water is equal to 1.33) | θc2 (Refractive index n2 of silicon oil is equal to 1.403) |
| --- | --- | --- | --- | --- |
| First glass | 1.9 | 31.8° | 44.4° | 47.6° |
| Polycarbonate | 1.59 | 39.0° | 56.8° | 61.9° |
| Polystyrene | 1.59 | 39.0° | 56.8° | 61.9° |
| Second glass | 1.5 | 41.8° | 62.5° | 69.3° |
| Methyl methacrylate | 1.49 | 42.2° | 63.2° | 70.3° |
| Epoxy resin | 1.48 | 42.5° | 64.0° | 71.4° |
| Quartz glass | 1.458 | 43.3° | 65.8° | 74.2° |
| Fluorinated ethylene propylene | 1.338 | 47.3° | 83.7° | (no total reflection) |

It should be appreciated for those skilled in this art that the above embodiments are intended to be illustrated, and not restrictive. For example, many modifications may be made to the above embodiments by those skilled in this art, and various features described in different embodiments may be freely combined with each other without conflicting in configuration or principle, so that more kinds of silicon oil sensors can be achieved with overcoming the technical problem of the present invention.

Although several exemplary embodiments have been shown and described, it would be appreciated by those skilled in the art that various changes or modifications may be made in these embodiments without departing from the principles and spirit of the disclosure, the scope of which is defined in the claims and their equivalents.

As used herein, an element recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

What is claimed is:

1. A silicon oil sensor, comprising:
   a transparent member having a light receiving passageway with an oil receiving section and a side surface; and
   a laser source emitting a laser beam into the light receiving passageway such that an incident angle θ of the laser beam (L) with respect to the side surface is selected so that a total reflection of the laser beam (L) occurs on the side surface when the oil receiving section is filled with air and when the oil receiving section is filled with water, and exits out of the transparent member along a total reflection path (L1), while a refraction of the laser beam (L) occurs along a refraction path (L2) when the oil receiving section collects silicon oil.

2. The silicon oil sensor according to claim 1, wherein the incident angle θ of the laser beam (L) with respect to the side surface meets the expression:

$\arc\sin(1/n1)=\theta c1 \leq \theta < \theta c2=\arc\sin(n2/n1)$, wherein n1 is a refractive index of the transparent member and n2 is a refractive index of the silicon oil, and n1 is greater than n2.

3. The silicon oil sensor according to claim 2, wherein the incident angle θ of the laser beam (L) with respect to the side surface meets the expression:

$\arc\sin(1/n1)=\theta c1 \leq \theta < 90°$, wherein n1 is less than n2.

4. The silicon oil sensor according to claim 3, wherein the θc1 is a critical angle at which the laser beam (L) directed into the transparent member is a total reflection on an interface between the transparent member and the air.

5. The silicon oil sensor according to claim 4, wherein the θc2 is a critical angle at which the laser beam (L) directed into the transparent member is a total reflection on an interface between the transparent member and the silicon oil.

6. The silicon oil sensor according to claim 5, wherein a refractive index of the air is equal to 1.

7. The silicon oil sensor according to claim 6, wherein the incident angle θ of the laser beam (L) with respect to the side surface meets the expression:

$\arc\sin(n3/n1)=\theta c3 \leq \theta < \theta c2$, wherein n1 is greater than n2, and n3 is the refractive index of water.

8. The silicon oil sensor according to claim 7, wherein the incident angle θ of the laser beam (L) with respect to the side surface meets the expression:

$\arc\sin(n3/n1)=\theta c3 \leq \theta < 90°$, wherein n1 is less than n2.

9. The silicon oil sensor according to claim 8, wherein θc3 is a critical angle at which the laser beam (L) directed into the transparent member is a total reflection on an interface between the transparent member and the water.

10. The silicon oil sensor according to claim 9, wherein n3 is less than n1 and n2.

11. The silicon oil sensor according to claim 1, wherein the side surface of the light receiving passageway faces the laser beam (L) and is a sloped side surface or a vertical side surface with respect to a length of the transparent member.

12. The silicon oil sensor according to claim 1, further comprising a first light detection device disposed at a first position corresponding to the total reflection path (L1) so as to receive the light of the laser beam (L) led out the transparent member along the total reflection path (L1).

13. The silicon oil sensor according to claim 12, further comprising a second light detection device disposed at a second position corresponding to the refraction path (L2) so as to receive the light of the laser beam (L) led out the transparent member along the refraction path (L2).

14. A silicon oil sensor, comprising:
   a transparent member having a light receiving passageway with an oil receiving section and a side surface;
   a laser source emitting a laser beam into the light receiving passageway such that an incident angle θ of the laser beam (L) with respect to the side surface is selected so that a total reflection of the laser beam (L) occurs on the side surface when the oil receiving section is filled with air and exits out of the transparent member along a total reflection path (L1), while a refraction of the laser beam (L) occurs along a refraction path (L2) when the oil receiving section collects silicon oil; and
   a light detection device disposed at a position corresponding to the refraction path (L2) so as to receive the light of the laser beam (L) led out the transparent member along the refraction path (L2).

* * * * *